(12) United States Patent
Austring

(10) Patent No.: US 11,907,248 B2
(45) Date of Patent: Feb. 20, 2024

(54) SYSTEM AND METHOD OF IMMUTABLE ELECTRONIC HEALTH RECORD DATA STORAGE

(71) Applicant: Technologies IP, LLC, Fort Worth, TX (US)

(72) Inventor: Ronald Raymond Austring, English Harbour (AG)

(73) Assignee: Technologies IP, LLC, Fort Worth, TX (US)

( * ) Notice: Subject to any disclaimer, the term of this patent is extended or adjusted under 35 U.S.C. 154(b) by 16 days.

(21) Appl. No.: 17/730,804

(22) Filed: Apr. 27, 2022

(65) Prior Publication Data

US 2022/0342906 A1    Oct. 27, 2022

Related U.S. Application Data

(60) Provisional application No. 63/201,388, filed on Apr. 27, 2021, provisional application No. 63/201,386, (Continued)

(51) Int. Cl.
| | |
|---|---|
| G06F 16/20 | (2019.01) |
| G06F 16/25 | (2019.01) |
| H04L 9/00 | (2022.01) |
| G06Q 20/06 | (2012.01) |
| G06Q 20/12 | (2012.01) |
| G06Q 20/36 | (2012.01) |
| G16H 10/60 | (2018.01) |

(Continued)

(52) U.S. Cl.
CPC .......... *G06F 16/258* (2019.01); *G06F 16/27* (2019.01); *G06F 21/6245* (2013.01); *G06Q 20/065* (2013.01); *G06Q 20/1235* (2013.01); *G06Q 20/367* (2013.01); *G06Q 30/0283* (2013.01); *G16H 10/60* (2018.01); *H04L 9/50* (2022.05); *G06F 2221/2141* (2013.01); *H04L 2209/56* (2013.01)

(58) Field of Classification Search
None
See application file for complete search history.

(56) References Cited

U.S. PATENT DOCUMENTS

| | | |
|---|---|---|
| 2014/0136237 A1 | 5/2014 | Anderson et al. |
| 2016/0004820 A1 | 1/2016 | Moore |

(Continued)

OTHER PUBLICATIONS

PCT International Appl. No. PCT/US22/26593 International Search Report and Written Opinion, 7 pages, dated Aug. 26, 2022.

*Primary Examiner* — Belix M Ortiz Ditren
(74) *Attorney, Agent, or Firm* — Whitaker Chalk Swindle & Schwartz, PLLC; Enrique Sanchez, Jr.; Juan Vazquez

(57) ABSTRACT

A system and method of immutable electronic health record data storage is presented. The present disclosure provides for a system integrated into a practical application with meaningful limitations to provide a system having an 'immutable data storage protocol' used to capture database operations on an immutable ledger. The protocol can consist of one or more 'operation codes.' The immutable electronic health record data storage system can provide a blockchain, transaction blockchain API, a blockchain writer API, a formatting module, and a messaging module, among others, that can format, process, and store data according to an immutable data storage protocol.

20 Claims, 5 Drawing Sheets

Related U.S. Application Data filed on Apr. 27, 2021, provisional application No. 63/201,387, filed on Apr. 27, 2021, provisional application No. 63/201,383, filed on Apr. 27, 2021, provisional application No. 63/201,385, filed on Apr. 27, 2021.

(51) Int. Cl.
*G06F 21/62* (2013.01)
*G06Q 30/0283* (2023.01)
*G06F 16/27* (2019.01)

(56) References Cited

U.S. PATENT DOCUMENTS

| | | |
|---|---|---|
| 2017/0161435 A1 | 6/2017 | Orosco |
| 2019/0354693 A1 | 11/2019 | Yoon et al. |
| 2020/0012676 A1 | 1/2020 | Narang et al. |
| 2020/0210404 A1* | 7/2020 | Kain ................. G16H 10/60 |
| 2020/0226285 A1* | 7/2020 | Bulleit ................ G06F 21/33 |
| 2020/0320061 A1 | 10/2020 | Korpman et al. |
| 2020/0402624 A1* | 12/2020 | Austring ............. G07F 11/10 |
| 2021/0075623 A1* | 3/2021 | Petersen .............. H04L 9/50 |

* cited by examiner

SYSTEM AND METHOD OF IMMUTABLE ELECTRONIC HEALTH RECORD DATA STORAGE

CROSS-REFERENCE TO RELATED APPLICATIONS

The present application claims priority to U.S. Provisional Patent Application Ser. No. 63/201,383, filed on Apr. 27, 2021, entitled "ADDRESSABLE UNIVERSAL DATA LOCATOR SYSTEM FOR PROGRAM EXECUTION AND METHOD THEREFOR," U.S. Provisional Patent Application Ser. No. 63/201,385, filed on Apr. 27, 2021, entitled "ELECTRONIC HEALTH RECORD PERMISSIONING SYSTEM AND METHOD," U.S. Provisional Patent Application Ser. No. 63/201,388, filed on Apr. 27, 2021, entitled "ELECTRONIC HEALTH RECORD DATA QUALIFICATION SYSTEM AND METHOD," U.S. Provisional Patent Application Ser. No. 63/201,387, filed on Apr. 27, 2021, entitled "SERVER PROTOCOL FORMATTING SYSTEM AND METHOD," and U.S. Provisional Patent Application Ser. No. 63/201,386, filed on Apr. 27, 2021, entitled "PROPERTY COLLECTION SYSTEM AND METHOD," the contents of which are incorporated herein in their entireties for all purposes.

TECHNICAL FIELD

The present disclosure generally relates to record data storage, and more specifically to systems and methods of immutable electronic health record data storage on a blockchain.

BACKGROUND

The current state of a data record is a reflection of all the database operations that have occurred on the data record from its original writing. For example, if a 'Patient' record has been written to a database, as changes are made to the 'Patient' record, database 'update' operations are used to apply these changes and overwrite any previous values for the columns being updated. During these operations all history of the changes are lost unless database operation logging has been enabled for the database. Database operation logging is used for data recovery purposes and should not be considered as an immutable history of the database operations that occurred on the database. Immutable storage technology, such as blockchain, by its very nature does not allow update or delete operations on data. Once a data item has been written it can never be changed. In order to achieve true immutable database operation history a 'distributed ledger technology' (DLT) must be used to record the database operations. Currently the only implementation of DLT that meets the requirement of true immutability is blockchain technology based on 'proof of work' (POW) consensus, which incentivizes miners with profitable transaction fees, and has an open membership in a public network.

SUMMARY

The present disclosure achieves technical advantages as a system and method of immutable electronic health record data storage. The present disclosure provides for a system integrated into a practical application with meaningful limitations to provide a system having an 'immutable data storage protocol' used to capture database operations on an immutable ledger. The protocol can consist of one or more 'operation codes.'

The present disclosure solves the technological problem of overwriting of database operations that have occurred on the data record from its original writing. The immutable electronic health record data storage system solves the aforementioned technological problem by providing a blockchain, transaction blockchain API, formatting module, and a messaging module, among others that can format, process, and store data according to an immutable data storage protocol. Such modules can be implemented in one or more servers coupled to memory (local, network, distributed, or otherwise). Accordingly, the claims herein are necessarily rooted in computer technology as they overcome a problem arising in the realm of computer database storage, access, and data transmission.

The present disclosure provides a technological solution missing from conventional systems by providing a system that can implement an immutable data storage protocol (IDSP) that can be used to record meta data, data operations, and the data that is being written to an immutable storage technology. Additionally, the system can serialize a Property Collection for storage on a blockchain according to the principles disclosed herein.

Accordingly, the present disclosure discloses concepts inextricably tied to computer technology such that the present disclosure provides the technological benefit of optimizing database technology to format and store data on a blockchain without the need for costly blockchain "mining" systems that require immense power, processing capability, and facility space. The present disclosure technologically surpasses conventional technology as the present disclosure allows for immutable data storage via an immutable data storage protocol. The concepts taught by the present disclosure can be used in any data-centric industry but are particularly relevant in the healthcare industry (e.g. clinical, pharmaceutical, etc.).

It is an object of the invention to provide a system for immutable electronic health record data storage. It is a further object of the invention to provide a method of immutable electronic health record data storage. These and other objects are provided by the present disclosure, including at least the following embodiments.

In one embodiment, a system for immutable electronic health record data storage can include: a blockchain storing one or more property collections; and a computer processor operably coupled to the blockchain and capable of executing machine-readable instructions to perform program steps, the program steps comprising: receiving a first property collection having one or more fields to be written to the blockchain; serializing, via a blockchain writer API, at least a portion of the first property collection; determining, via the processor, the data operation code for the first property collection; appending immutable data storage protocol data, including the data operation code, to the serialized property collection; and writing the immutable data storage protocol data and the serialized property collection to the blockchain. Wherein the data operation code identifies the current state of the property collection. Wherein the immutable data storage protocol data includes metadata to identify information associated with the context of the data. Wherein the metadata includes data indicating when an operation occurred, an identity of an entity executing the operation, and a source of the operation. The program steps further comprising determining the data operation code is 'insert' and serializing the entire first property collection. The program steps further comprising determining the data operation code is 'update' and serializing only the fields updated in the first property collection. The program steps further comprising determining the data operation code is 'append' and serializing only the new fields in the first property collection. The program steps further comprising determining the data operation code is 'overwrite' and serializing the entire first property collection. The program steps further comprising determining the data operation code is 'delete' and serializing only the deleted fields in the first property collection. Wherein the deleted fields are set to null prior to serialization.

In another embodiment, a system for immutable electronic health record data storage can include: receiving a first property collection having one or more fields to be written to a blockchain; serializing, via a blockchain writer API, at least a portion of the first property collection; determining, via a processor, the data operation code for the first property collection; appending immutable data storage protocol data, including the data operation code, to the serialized property collection; and writing the immutable data storage protocol data and the serialized property collection to the blockchain. Wherein the data operation code identifies the current state of the property collection. Wherein the immutable data storage protocol data includes metadata to identify information associated with the context of the data. Wherein the metadata includes data indicating when an operation occurred, an identity of an entity executing the operation, and a source of the operation. Further comprising determining the data operation code is 'insert' and serializing the entire first property collection. Further comprising determining the data operation code is 'update' and serializing only the fields updated in the first property collection. Further comprising determining the data operation code is 'append' and serializing only the new fields in the first property collection. Further comprising determining the data operation code is 'overwrite' and serializing the entire first property collection. Further comprising determining the data operation code is 'delete' and serializing only the deleted fields in the first property collection. Wherein the deleted fields are set to null prior to serialization.

BRIEF DESCRIPTION OF THE DRAWINGS

The present disclosure will be readily understood by the following detailed description, taken in conjunction with the accompanying drawings that illustrate, by way of example, the principles of the present disclosure. The drawings illustrate the design and utility of one or more exemplary embodiments of the present disclosure, in which like elements are referred to by like reference numbers or symbols. The objects and elements in the drawings are not necessarily drawn to scale, proportion, or precise positional relationship. Instead, emphasis is focused on illustrating the principles of the present disclosure.

DETAILED DESCRIPTION

The disclosure presented in the following written description and the various features and advantageous details thereof, are explained more fully with reference to the non-limiting examples included in the accompanying drawings and as detailed in the description. Descriptions of well-known components have been omitted to not unnecessarily obscure the principal features described herein. The examples used in the following description are intended to facilitate an understanding of the ways in which the disclosure can be implemented and practiced. A person of ordinary skill in the art would read this disclosure to mean that any suitable combination of the functionality or exemplary embodiments below could be combined to achieve the subject matter claimed. The disclosure includes either a representative number of species falling within the scope of the genus or structural features common to the members of the genus so that one of ordinary skill in the art can recognize the members of the genus. Accordingly, these examples should not be construed as limiting the scope of the claims.

A person of ordinary skill in the art would understand that any system claims presented herein encompass all of the elements and limitations disclosed therein, and as such, require that each system claim be viewed as a whole. Any reasonably foreseeable items functionally related to the claims are also relevant. Pursuant to Section 904 of the Manual of Patent Examination Procedure, the Examiner, after having obtained a thorough understanding of the invention disclosed and claimed in the nonprovisional application has searched the prior art as disclosed in patents and other published documents, i.e., nonpatent literature. Therefore, as evidenced by the issuance of this patent, the prior art fails to disclose or teach the elements and limitations presented in the claims as enabled by the specification and drawings, such that the presented claims are patentable under 35 U.S.C. §§ 101, 102, 103, and 112.

Figure 1:
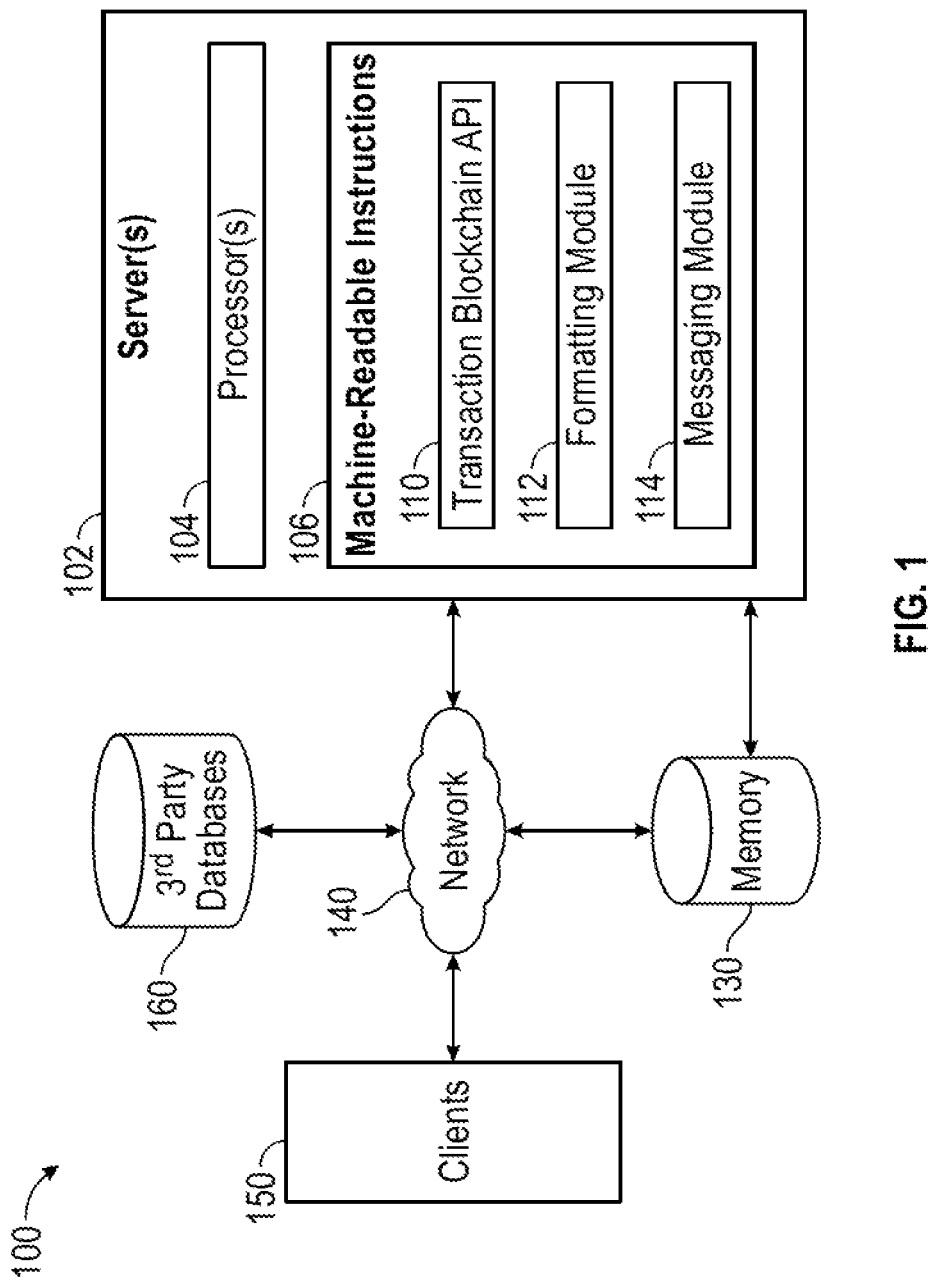
FIG. 1 illustrates an immutable electronic health record data storage system schematic, in accordance with one or more exemplary embodiments of the present disclosure.

FIG. 1 illustrates a schematic view of an immutable electronic health record data storage 100, in accordance with one or more exemplary embodiments of the present disclosure. The system 100 can include one or more servers 102 having one or more processors 104, a memory 130, machine readable instructions 106, including transaction blockchain API 110, a formatting module 112, and a messaging module 114, among other relevant modules. The server 102 can be operably coupled to one or more clients 150 via a network 140. The clients 150 can be a physical device (e.g., mobile phone, laptop, tablet, desktop computer, wearable device, or other suitable device), program, or application. In another exemplary embodiment, a client 150 can include a mobile phone having a mobile application configured to communicate with the server 102 over the network 140.

In one embodiment, a transaction blockchain API 110 can be provided by the system 100 for accessing the blockchain, the transaction blockchain API 110 having an interface that defines interactions between multiple components. For example, the blockchain API 110 can define the kinds of calls or requests that can be made, how to make them, the data formats that should be used, the conventions to follow, and other suitable functionality related to a blockchain. In another embodiment, the blockchain API 110 can access and retrieve Property Collections.

In one embodiment, a formatting module 112 can serialize data for storage on a blockchain and append metadata to the data to be stored on the blockchain. For example, the metadata can include one or more operation codes. In another embodiment, an 'operation code' can be an instruction capable of being interpreted by an 'immutable data reader' to build the current state of the data record. The 'operation codes' can be categorized as follows:

Meta Data
UTC Timestamp
Record ID
Source ID
Data Operation:
Insert
Update
Append
Overwrite
Delete
Data
A serialized 'Property Collection'.

In one embodiment, the 'meta data' operation codes can be used to capture information associated with the 'context' of the data, such as when the operation occurred (e.g., UTC Timestamp), the identity of an entity (e.g., Record ID) and the source of the database operation (e.g., Source ID).

In another embodiment, the 'data operation' operation codes can be used to capture the database operation taking place, for example, in one embodiment:

Insert—can indicate a new 'data entity' has been created;
Update—can indicate specific properties of a 'data entity' have been updated;
Append—can indicate a new property has been added to a 'data entity;'
Overwrite—can indicate a several property values of a data entity have changed and it has been determined to record the current state of the entity as opposed to the incremental changes (this operation contains the same data as an 'Insert' operation but implies that the data is being rewritten); and
Delete—can indicate a 'data entity' was deleted.

In another embodiment, the 'Data' operation code can indicate a serialized property collection. For example, a 'Property Collection' can be a collection of 'property name' and 'property value' pairs, which can be used to describe a 'data entity.' A property value can contain a: 'String,' 'Integer,' 'Decimal,' 'Date,' 'Time,' 'DateTime,' 'Boolean,' 'Byte Array,' a 'Property Collection Reference' (e.g., reference to another Property Collection), or an array of 'Property Collection References.' A 'Property Collection' can be persisted/converted into various forms of memory representations and/or media (e.g., JSON object, flat file, database, cache, immutable storage technology, etc.). In another embodiment, the 'Property Collection' can be serialized to a 'byte array.' A properties value can be retrieved from a 'Property Collection' using a technology known as a 'property path.' A 'property path' can be an ASCII string used to access a 'property value.' A 'property path' can be used to access a 'property value' in a nested 'property collection.' For example, a patient's zip code could be accessed with the following string: "Patient.Address.Zip."

In one embodiment, a messaging module 114 can transmit data structured according to the immutable storage protocol to the blockchain. For example, messaging module 114 can open one or more channels to the blockchain via the transaction blockchain API 110 to transmit the serialized Property Collection 'byte array' to the transaction blockchain API 110 for storage on the blockchain.

The aforementioned systems, components, and modules can be communicably coupled to each other via the network 140, such that data can be transmitted therebetween. The network 140 can be the Internet, intranet, computer bus, or other suitable network. The data transmission can be encrypted, unencrypted, over a VPN tunnel, or other suitable communication means. The network 140 can be a WAN, LAN, PAN, or other suitable network type. The network communication can be encrypted using PGP, Blowfish, Twofish, AES, 3DES, HTTPS, or other suitable encryption. The system 100 can be configured to provide communication via the various systems, components, and modules disclosed herein via an application programming interface (API), PCI, PCI-Express, ANSI-X12, Ethernet, Fiber, Wi-Fi, Bluetooth, or other suitable communication protocol or medium. Additionally, third party systems and databases 160 can be operably coupled to the system components via the network 140.

The data transmitted to and from the components of system 100 (e.g., the server 102, memory 130, and clients 150), can include any format, including the XPP format disclosed herein, JavaScript Object Notation (JSON), TCP/IP, XML, HTML, ASCII, SMS, CSV, representational state transfer (REST), or other suitable format. The data transmission can include a message, flag, header, header properties, metadata, and/or a body, or be encapsulated and packetized by any suitable format having same.

The server(s) 102 can be implemented in hardware, software, or a suitable combination of hardware and software therefor, and may comprise one or more software systems operating on one or more servers, having one or more processors 104, with access to memory 130. Server(s) 102 can include electronic storage, one or more processors, and/or other components. Server(s) 102 can include communication lines, connections, and/or ports to enable the exchange of information via a network 140 and/or other computing platforms. Server(s) 102 can also include a plurality of hardware, software, and/or firmware components operating together to provide the functionality attributed herein to server(s) 102. For example, server(s) 102 can be implemented by a cloud of computing platforms operating together as server(s) 102, including Software-as-a-Service (SaaS) and Platform-as-a-Service (PaaS) functionality. Additionally, the server(s) 102 can include memory 130, locally attached, network attached, or both.

Memory 130 can comprise electronic storage that can include non-transitory storage media that electronically stores information. The electronic storage media of electronic storage can include one or both of system storage that can be provided integrally (e.g., substantially non-removable) with server(s) 102 and/or removable storage that can be removably connectable to server(s) 102 via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). The electronic storage can include a database, or public or private distributed ledger (e.g., blockchain). In one embodiment, memory 130 can be a blockchain implemented on one or more platforms, including BigChainDB, nChain, Ethereum, Hyperledger, R3, Ripple, EOS, or other suitable blockchain platform. The blockchain can be a public blockchain (accessible to the general public) or a private blockchain (accessible only by those parties credentialed for access). Electronic storage can store machine-readable instructions 106, software algorithms, control logic, data generated by processor(s), data received from server(s), data received from computing platform(s), and/or other data that can enable server(s) to function as described herein. The electronic storage can also include third-party databases accessible via the network 140.

Processor(s) 104 can be configured to provide data processing capabilities in server(s) 102. As such, processor(s) 104 can include one or more of a digital processor, an analog processor, a digital circuit designed to process information, an analog circuit designed to process information, a state machine, and/or other mechanisms for electronically processing information, such as FPGAs or ASICs. The processor(s) 104 can be a single entity or include a plurality of processing units. These processing units can be physically located within the same device, or processor(s) 104 can represent processing functionality of a plurality of devices or software functionality operating alone, or in concert.

The processor(s) 104 can be configured to execute machine-readable instructions 106 or machine learning modules via software, hardware, firmware, some combination of software, hardware, and/or firmware, and/or other mechanisms for configuring processing capabilities on processor(s) 104. As used herein, the term "machine-readable instructions" can refer to any component or set of components that perform the functionality attributed to the machine-readable instructions component 106. This can include one or more physical processors 104 during execution of processor-readable instructions, the processor-readable instructions, circuitry, hardware, storage media, or any other components.

The server(s) 102 can be configured with machine-readable instructions having one or more functional modules. The machine-readable instructions 106 can be implemented on one or more servers 102, having one or more processors 104, with access to memory 130. The machine-readable instructions 106 can be a single networked node, or a machine cluster, which can include a distributed architecture of a plurality of networked nodes. The machine-readable instructions 106 can include control logic for implementing various functionality, as described in more detail below. The machine-readable instructions 106 can include certain functionality associated with the system 100. Additionally, the machine-readable instructions 106 can include a smart contract or multi-signature contract that can process, read, and write data to the memory 130, 3rd party database 160, including a database, distributed ledger, or blockchain.

Figure 4:
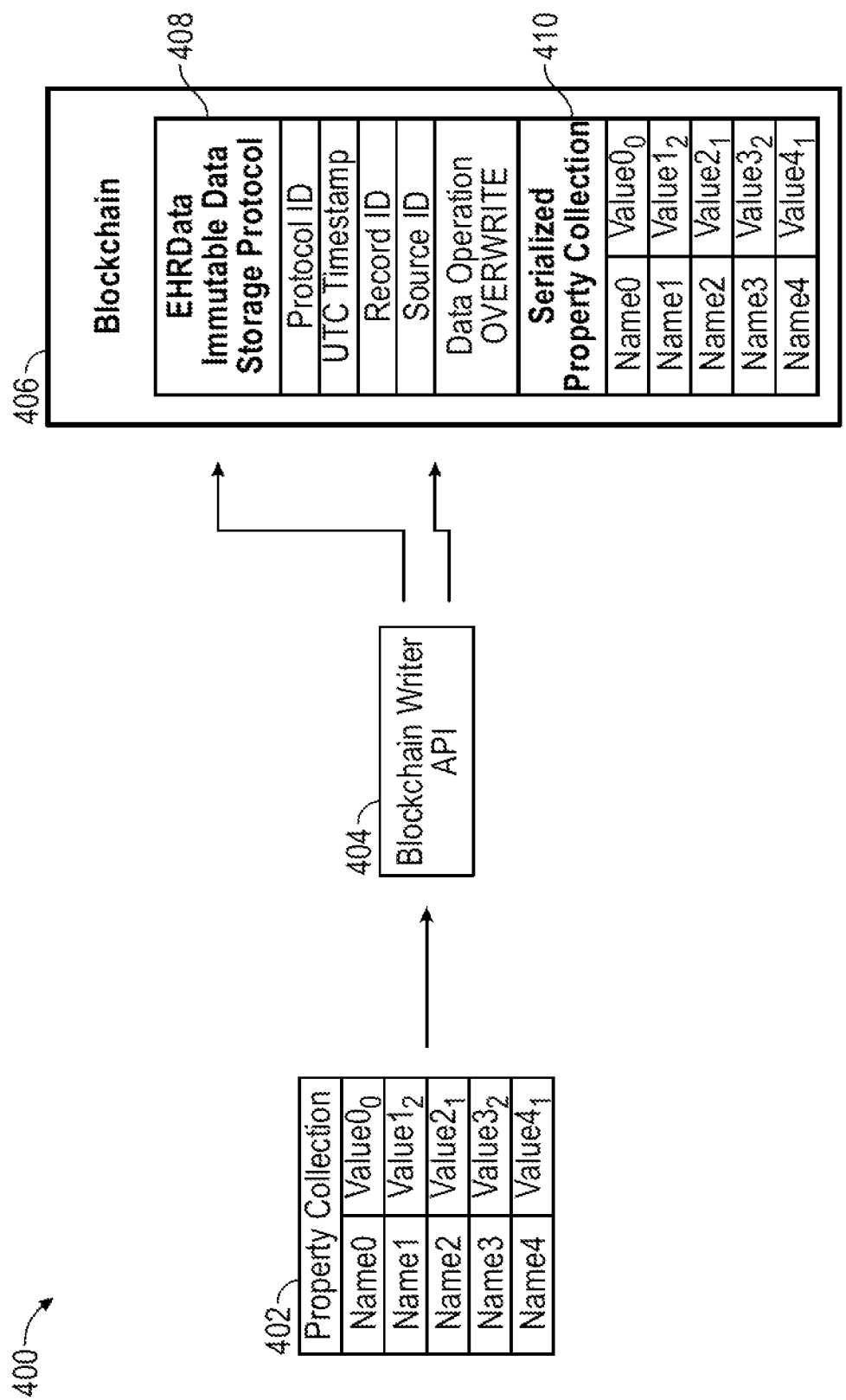
FIG. 4 illustrates an immutable electronic health record data storage system overwrite/insert operation schematic, in accordance with one or more exemplary embodiments of the present disclosure.

FIG. 4 illustrates an immutable electronic health record data storage system insert or overwrite operation 400 schematic, in accordance with one or more exemplary embodiments of the present disclosure. As the 'insert' and 'overwrite' operations contain the same data the two operations will be addressed using the same FIG. 4. The difference between the 'insert' and the 'overwrite' operation would be the data operation code listed in the immutable data storage protocol 408. In one embodiment, the overwrite operation code can imply that the data is being rewritten. In another embodiment, the immutable electronic health record data storage system insert or overwrite operation 400 can include a blockchain writer API 404. The blockchain writer API 404 can include one or more aspects of the transactional blockchain API 110, the formatting module 112, and the messaging module 114. The blockchain writer API 404 can be instantiated on one or more servers 102. The blockchain can be instantiated on memory 130.

In one embodiment, the blockchain writer API 404 can receive a Property Collection 402 having properties Name0, Name1, Name2, Name3, and Name4 with respective values of $Value0_0$, $Value1_2$, $Value2_1$, $Value3_2$, and $Value4_1$. In another embodiment, the blockchain writer API 404 can serialized the entire Property Collection 402 and write the serialized Property Collection 410 to the blockchain 406. In another embodiment, serialization can be the process of converting a 'Property Collection' into a 'byte array' such that the contents of the 'Property Collection' can be written to, and read from, a blockchain 406 in an efficient manner. For example, the Property Collection 402 can be serialized into a byte array.

In one embodiment, the serialized Property Collection 410 can be appended with an immutable data storage protocol 408 having one or more metadata and one or more operational codes. For example, the immutable data storage protocol 408 can include a Protocol ID, an UTC Timestamp, a Record ID, an Source ID, and a data operation code of 'Overwrite' or 'Insert.' The serialized 'Property Collection' 410 written is the same as the input property collection 402. The 'Overwrite' operation is used when the blockchain writer API 404 determines that it is more efficient to write all data rather than the incremental changes. The 'Overwrite' operation can be similar to an 'Insert' operation and used to inform a blockchain data reader that the data contained in the operation is the current state of the 'Property Collection.' Thereby effectively informing the blockchain data reader that all previous data operations, on the 'Property Collection' can be disregarded.

The immutable data storage protocol 408 can apply to any type of data related to the Property Collection. For example, clear text, encrypted data, or a hash of the Property Collection. For example, the data operation code can be 'insert' or 'overwrite.' Once written to the blockchain 410, the property collection can be identified using the identity of an entity (e.g., Record ID). Different blocks having the Record ID can be aggregate to reconstruct a complete history of the data record, including any additions, deletion, edits, insertions, etc., as no data can be removed from the blockchain 402 without corrupting the data, the data can be tagged to identify the operation performed, along with when it was performed.

By way of example, in one embodiment, given piece of data, such as a doctor's prescription for a particular patient, should someone seek to change that data such as a doctor wanting to change the dosage on a prescription after an overdose of a patient to avoid liability, such change is impossible at this point if the prescription data was written to a blockchain 402. For example, the blockchain writer API 404 can determine what portion of the data was changed, and can write a either a hash or the data to the blockchain to say that it's recording that change. So it's because it's immutable, such that no one can ever argue that the change didn't happen. Should the prescription data not have been written to a blockchain, the doctor could pay a programmer to go in the database and change the prescription and no one would know the difference. But because the original prescription was recorded on an immutable blockchain, it cannot be changed and cannot be challenged. As blockchain implements a consensus protocol of what gets written data stored in the blockchain cannot be altered at one node, as the other nodes can detect the change and flag the changed data us untrustworthy.

With regard to healthcare data, as patient data can be stored either directly on the blockchain or a hash of the patient data can be stored on the blockchain as a unique identifier to retrieve the data from a corresponding archival node. As a blockchain can be public, HIPPA regulations may prohibit the open storage of the patient data. If a hash of the data is written to the blockchain 406, a corresponding archival node can be utilized to retrieve the original patient data. So when the blockchain data is corrupted, due to, for example, an editing of stored data, the data can be retrieved from an archival node. But related to blockchain data storage, as the data history changes, the blockchain writer API 404 can write every incremental change to the blockchain or periodically batch the changes and write the batch to the blockchain. In this way the system can effectively provide an auditing tool to determine if there was a change, who changed it, and when they changed it, among other characteristics.

In another embodiment, the identifier can identify a piece of data as belong to an entity. The protocol ID can identify what a particular piece of data is within the entity data. The UTC timestamp can be the time when the data was written into the database, as it could be written to the blockchain at a different time, typically, every 10 minutes. But the property collection data could have been written to a database and the blockchain writer API 404 did not write it to the blockchain for several hours. The blockchain itself records when a block is written to the blockchain, but not when the data was originally written.

Figure 2:
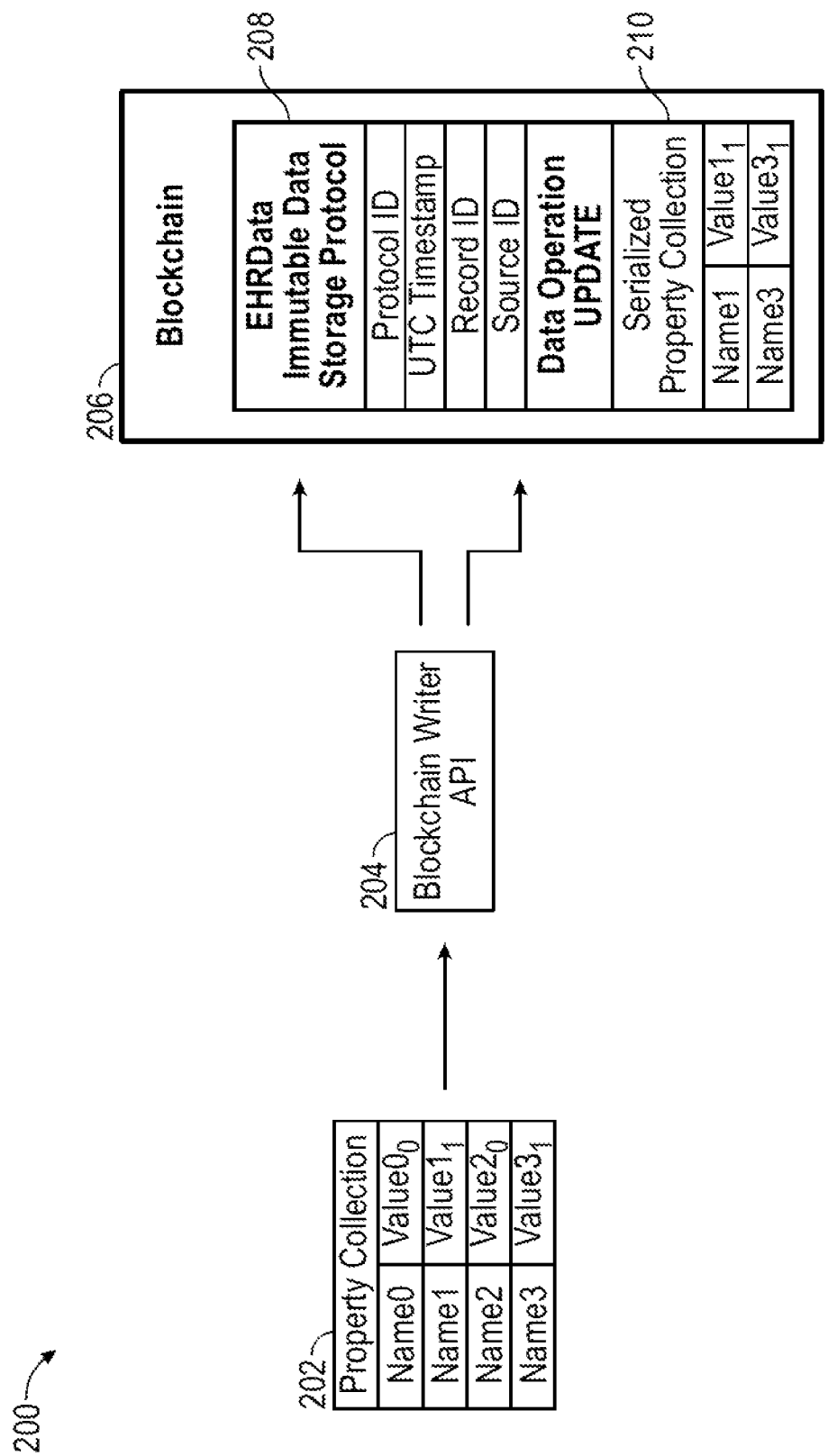
FIG. 2 illustrates an immutable electronic health record data storage system update operation schematic, in accordance with one or more exemplary embodiments of the present disclosure.

FIG. 2 illustrates an immutable electronic health record data storage system update operation 200 schematic, in accordance with one or more exemplary embodiments of the present disclosure. In another embodiment, the immutable electronic health record data storage system update operation 200 can include a blockchain writer API 204. The blockchain writer API 204 can include one or more aspects of the transactional blockchain API 110, the formatting module 112, and the messaging module 114. The blockchain writer API 204 can be instantiated on one or more servers 102. The blockchain can be instantiated on memory 130.

In one embodiment, the blockchain writer API 204 can receive a Property Collection 202 having properties Name0, Name1, Name2, and Name3 with respective values of Value$0_0$, Value$1_1$, Value$2_0$, and Value$3_1$. In another embodiment, the blockchain writer API 204 can serialized only the updated Property Collection 202 data and write the serialized Property Collection 210 updated data to the blockchain 206. In one embodiment, the serialized 'Property Collection' 210 written to the blockchain 206 only contains the fields in the 'Property Collection' that changed ('Name1' and 'Name3'). In another embodiment, the serialized Property Collection 210 can be appended with an immutable data storage protocol 208 having one or more metadata and one or more operational codes. For example, the immutable data storage protocol 208 can include a Protocol ID, an UTC Timestamp, a Record ID, an Source ID, and a data operation code of 'Update.'

Figure 3:
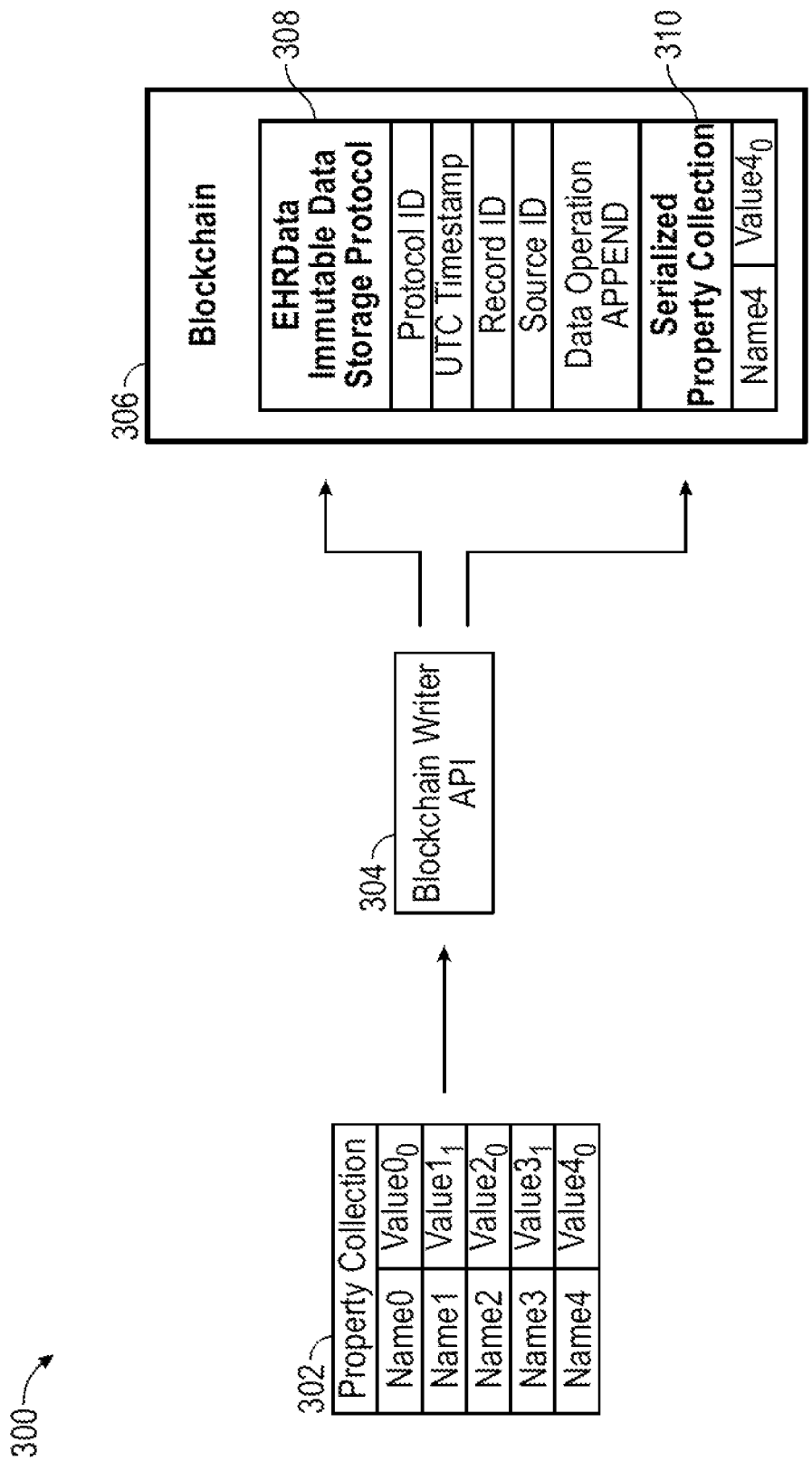
FIG. 3 illustrates an immutable electronic health record data storage system append operation schematic, in accordance with one or more exemplary embodiments of the present disclosure.

FIG. 3 illustrates an immutable electronic health record data storage system append operation 300 schematic, in accordance with one or more exemplary embodiments of the present disclosure. In another embodiment, the immutable electronic health record data storage system append operation 300 can include a blockchain writer API 304. The blockchain writer API 304 can include one or more aspects of the transactional blockchain API 110, the formatting module 112, and the messaging module 114. The blockchain writer API 304 can be instantiated on one or more servers 102. The blockchain can be instantiated on memory 130.

In one embodiment, the blockchain writer API 304 can receive a Property Collection 302 having properties Name0, Name1, Name2, Name3, and Name4 with respective values of Value$0_0$, Value$1_1$, Value$2_0$, Value$3_1$, and Value$4_0$. In another embodiment, the blockchain writer API 304 can serialized only the updated Property Collection 302 data and write the serialized Property Collection 310 updated data to the blockchain 306. In one embodiment, the serialized 'Property Collection' 310 written to the blockchain 306 only contains the new properties (e.g., Name4). In another embodiment, the serialized Property Collection 310 can be appended with an immutable data storage protocol 208 having one or more metadata and one or more operational codes. For example, the immutable data storage protocol 208 can include a Protocol ID, an UTC Timestamp, a Record ID, an Source ID, and a data operation code of 'Update.'

Figure 5:
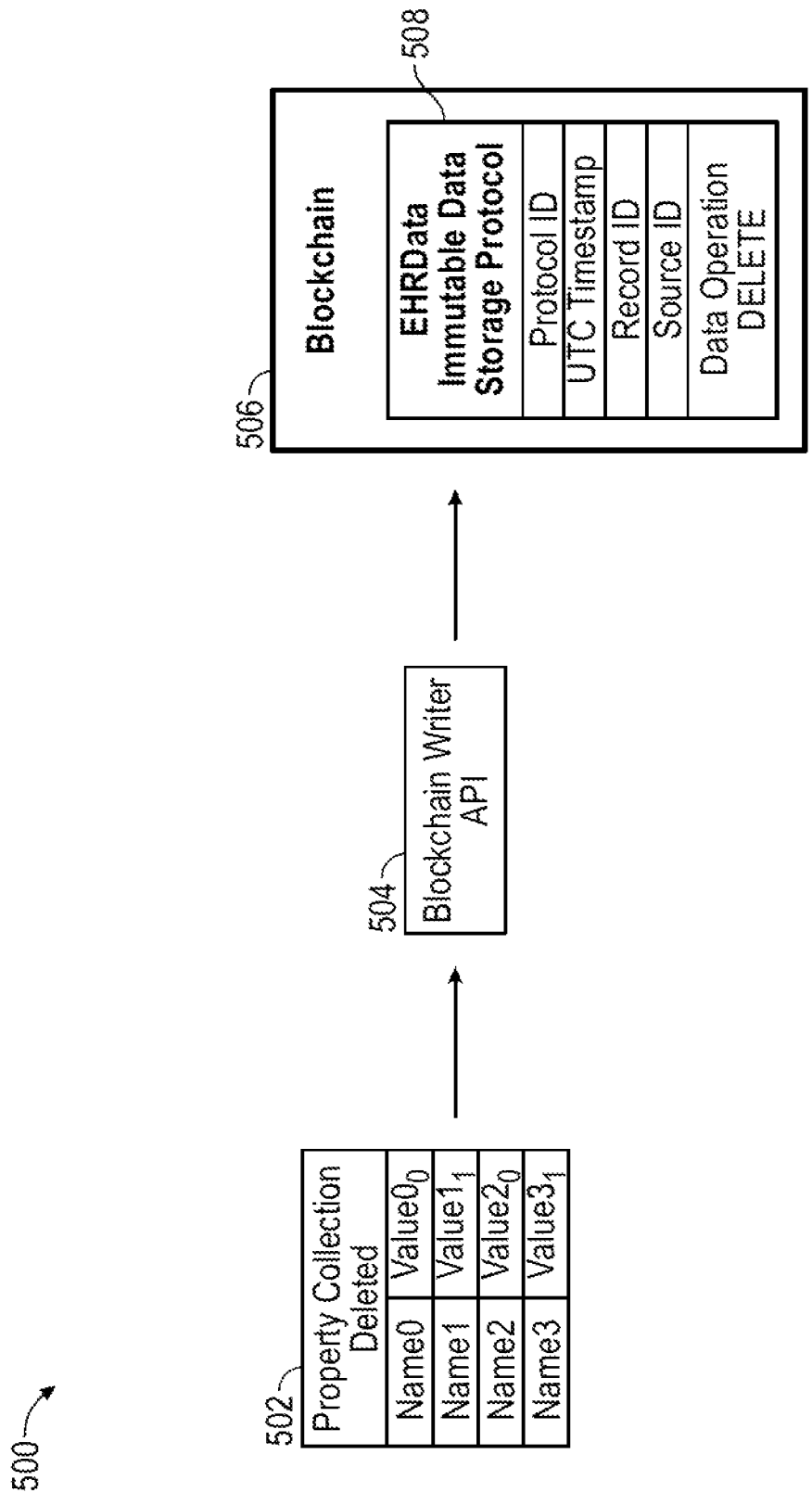
FIG. 5 illustrates an immutable electronic health record data storage system delete operation schematic, in accordance with one or more exemplary embodiments of the present disclosure.

FIG. 5 illustrates an immutable electronic health record data storage system delete operation 500 schematic, in accordance with one or more exemplary embodiments of the present disclosure. In another embodiment, the immutable electronic health record data storage system delete operation 500 can include a blockchain writer API 504. The blockchain writer API 504 can include one or more aspects of the transactional blockchain API 110, the formatting module 112, and the messaging module 114. The blockchain writer API 504 can be instantiated on one or more servers 102. The blockchain can be instantiated on memory 130.

In one embodiment, the blockchain writer API 504 can receive a Property Collection 502 to be deleted having properties Name0, Name1, Name2, and Name3 with respective values of Value$0_0$, Value$1_1$, Value$2_0$, and Value$3_1$. In another embodiment, the blockchain writer API 504 can delete an entire record and so no serialized Property Collection data exists as the entire 'Property Collection' is being deleted. For example, only the 'operation codes' used to capture the metadata may be written to the blockchain 506. In another embodiment, only a portion of the 'Property Collection' is being deleted, so the blockchain writer API 504 can receive and serialize the deleted properties and leave the deleted property values as the last were or set them to null. For example, the serialized 'Property Collection' would written to the blockchain 506. In another embodiment, the immutable data storage protocol 208 can have one or more metadata and one or more operational codes. For example, the immutable data storage protocol 208 can include a Protocol ID, an UTC Timestamp, a Record ID, an Source ID, and a data operation code of 'Update.'

Although one or more embodiments may reference a patient, the present disclosure applies to any type of entity, whether a person, patient, customer, company, or other suitable entity capable of having data stored in a record associated with that entity. Similarly, although certain embodiments may reference electronic health records, the systems, methods, and concepts disclosed herein are equally applicable to any storage system or record type.

Persons skilled in the art will readily understand that advantages and objectives described above would not be possible without the particular combination of computer hardware and other structural components and mechanisms assembled in this inventive system and described herein. Additionally, the algorithms, methods, and processes disclosed herein improve and transform any general-purpose computer or processor disclosed in this specification and drawings into a special purpose computer programmed to perform the disclosed algorithms, methods, and processes to achieve the aforementioned functionality, advantages, and objectives. It will be further understood that a variety of programming tools, known to persons skilled in the art, are available for generating and implementing the features and operations described in the foregoing. Moreover, the particular choice of programming tool(s) may be governed by the specific objectives and constraints placed on the implementation selected for realizing the concepts set forth herein and in the appended claims.

The description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f). Even under the broadest reasonable interpretation, in light of this paragraph of this specification, the claims are not intended to invoke 35 U.S.C. § 112(f) absent the specific language described above.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A system for immutable electronic health record data storage, comprising:
   a blockchain storing one or more property collections; and
   a computer processor operably coupled to the blockchain and capable of executing machine-readable instructions to perform program steps, the program steps comprising:
      receiving a first property collection having one or more fields to be written to the blockchain;
      serializing, via a blockchain writer API, at least a portion of the first property collection;
      determining, via the processor, the data operation code for the first property collection;
      appending immutable data storage protocol data, including the data operation code, to the serialized property collection; and
      writing the immutable data storage protocol data and the serialized property collection to the blockchain.

2. The system of claim 1, wherein the data operation code identifies the current state of the property collection.

3. The system of claim 1, wherein the immutable data storage protocol data includes metadata to identify information associated with the context of the data.

4. The system of claim 3, wherein the metadata includes data indicating when an operation occurred, an identity of an entity executing the operation, and a source of the operation.

5. The system of claim 1, the program steps further comprising determining the data operation code is 'insert' and serializing the entire first property collection.

6. The system of claim 1, the program steps further comprising determining the data operation code is 'update' and serializing only the fields updated in the first property collection.

7. The system of claim 1, the program steps further comprising determining the data operation code is 'append' and serializing only the new fields in the first property collection.

8. The system of claim 1, the program steps further comprising determining the data operation code is 'overwrite' and serializing the entire first property collection.

9. The system of claim 1, the program steps further comprising determining the data operation code is 'delete' and serializing only the deleted fields in the first property collection.

10. The system of claim 9, wherein the deleted fields are set to null prior to serialization.

11. A method of immutable electronic health record data storage, comprising:
    receiving a first property collection having one or more fields to be written to a blockchain;
    serializing, via a blockchain writer API, at least a portion of the first property collection;
    determining, via a processor, the data operation code for the first property collection;
    appending immutable data storage protocol data, including the data operation code, to the serialized property collection; and
    writing the immutable data storage protocol data and the serialized property collection to the blockchain.

12. The method of claim 11, wherein the data operation code identifies the current state of the property collection.

13. The method of claim 11, wherein the immutable data storage protocol data includes metadata to identify information associated with the context of the data.

14. The method of claim 13, wherein the metadata includes data indicating when an operation occurred, an identity of an entity executing the operation, and a source of the operation.

15. The method of claim 11, further comprising determining the data operation code is 'insert' and serializing the entire first property collection.

16. The method of claim 11, further comprising determining the data operation code is 'update' and serializing only the fields updated in the first property collection.

17. The method of claim 11, further comprising determining the data operation code is 'append' and serializing only the new fields in the first property collection.

18. The method of claim 11, further comprising determining the data operation code is 'overwrite' and serializing the entire first property collection.

19. The method of claim 11, further comprising determining the data operation code is 'delete' and serializing only the deleted fields in the first property collection.

20. The method of claim 19, wherein the deleted fields are set to null prior to serialization.

\* \* \* \* \*